(12) United States Patent
Barbur et al.

(10) Patent No.: US 8,322,857 B2
(45) Date of Patent: Dec. 4, 2012

(54) VISION TESTING APPARATUS AND METHOD

(76) Inventors: John Lazar Barbur, London (GB);
Jonathan Alister Harlow, London (GB)

( * ) Notice: Subject to any disclaimer, the term of this patent is extended or adjusted under 35 U.S.C. 154(b) by 0 days.

(21) Appl. No.: 12/665,054

(22) PCT Filed: Jun. 18, 2008

(86) PCT No.: PCT/GB2008/002081
§ 371 (c)(1),
(2), (4) Date: Dec. 17, 2009

(87) PCT Pub. No.: WO2008/155544
PCT Pub. Date: Dec. 24, 2008

(65) Prior Publication Data
US 2010/0165294 A1   Jul. 1, 2010

(30) Foreign Application Priority Data
Jun. 18, 2007   (GB) .................................. 0711738.5

(51) Int. Cl.
*A61B 3/02*   (2006.01)
(52) U.S. Cl. ........................................ 351/223; 351/239
(58) Field of Classification Search ........... 351/200–246
See application file for complete search history.

(56) References Cited

U.S. PATENT DOCUMENTS

| | | | |
|---|---|---|---|
| 5,898,419 A | 4/1999 | Wai Liu | |
| 6,033,076 A * | 3/2000 | Braeuning et al. | 351/224 |
| 6,111,573 A | 8/2000 | McComb et al. | |
| 6,386,707 B1 * | 5/2002 | Pellicano | 351/246 |
| 6,406,437 B1 * | 6/2002 | Zur et al. | 600/558 |
| 7,233,312 B2 * | 6/2007 | Stern et al. | 345/156 |
| 7,367,675 B2 * | 5/2008 | Maddalena et al. | 351/237 |
| 8,061,839 B2 * | 11/2011 | Frisen | 351/202 |
| 2009/0153803 A1 * | 6/2009 | Frisen | 351/239 |

FOREIGN PATENT DOCUMENTS

| | | |
|---|---|---|
| EP | 1767155 A | 3/2007 |
| WO | WO-0201321 A | 1/2002 |

OTHER PUBLICATIONS

European Patent Office, International Search Report for Application No. PCT/GB2008/002081, pp. 1-2 (Sep. 19, 2008).

* cited by examiner

*Primary Examiner* — Mohammed Hasan
(74) *Attorney, Agent, or Firm* — Modern Times Legal; Robert J. Sayre (57) ABSTRACT

An embodiment of the invention relates to vision testing apparatus comprising: a local display (9); means (13) for obtaining data characterising the performance characteristics of said local display; means (9) for displaying to a user at said local display, a vision test that comprises an adaptation of a reference vision test; means (11) for registering user input in response to said displayed vision test; and means (9) for providing the user with the results of said displayed test; wherein said reference vision test comprises a test that is optimised for display on a high quality display, and the vision test for display at said local display is obtained by adapting said reference test in accordance with said characterising data so that the vision test displayed on said local display is a faithful reproduction of said reference test.

15 Claims, 4 Drawing Sheets

VISION TESTING APPARATUS AND METHOD

FIELD OF THE INVENTION

This invention relates to vision testing, for example testing to assess visual performance. Particularly preferred embodiments of the invention relate to a method for measuring visual sensitivity and to apparatus for implementing that method. By way of example, such testing can prove to be useful in assessing minimum vision requirements in specified occupational environments and for detecting changes in visual sensitivity caused by disease or for monitoring the outcome of treatment.

BACKGROUND TO THE INVENTION

A variety of occupational, visual tests have previously been proposed for the assessment of various aspects of visual performance. For example, colour vision screening has previously been used as a means for detecting colour deficiencies, and as a means for assessing the severity of a user's colour vision loss.

Colour vision testing has also been used to determine whether a user's vision meets the colour vision requirements for a given occupation (for example: aviation, fire, transport or police services); to assist in the detection of diseases (such as diabetes or multiple sclerosis, for example) that can affect visual performance; to assist in the diagnosis of specific diseases of the eye (e.g., optic neuritis, age related macular degeneration, photoreceptor dystrophies, etc); to facilitate disease management and treatment monitoring, and to enable the monitoring of eye-related side-effects in drug trials.

One illustrative vision test that has previously been proposed is described in a paper entitled "New test to assess pilot's vision following refractive surgery" by C. M. Chisholm, A. D. Evans, J. A. Harlow, and J. L. Barbur (published in: Aviation, Space and Environmental Medicine 2003 May; 74(5): pages 551-559). The test described in this paper assessed the quality of spatial vision by using a Contrast Acuity Assessment (CAA) test at normal levels of ambient light (i.e., photopic vision). In essence, this test assessed the quality of achromatic vision by measuring the smallest luminance contrast needed to resolve and locate the position of a gap in an annulus.

Another illustrative, classic vision test involves the measurement of high contrast Visual Acuity (VA). In this test, a user is asked to locate the orientation of the gap in a Landolt C optotype, and the user's visual acuity is assessed on the basis of the smallest, high contrast Landolt C for which the user can resolve and locate the orientation of the gap. The test is carried out with both bright and dark targets and the results provide a measure of visual acuity similar to that measured with Snellen letter charts in optometric practices, but with improved accuracy and the use of a single target. The test can also be used to assess the effect of "visual crowding" when the test target is surrounded by other targets.

Yet another illustrative vision test is described in a paper entitled "Insights into the different exploits of colour in the visual cortex" by J. L. Barbur, A. J. Harlow, and G. T. Plant. (published in Proc. R. Soc. Lond. B. Biol. Sci. 258 (1353): 327-334, 19944). The test described in this paper used CAD (Colour Assessment & Diagnosis) to measure red-green and yellow-blue chromatic sensitivity. The paper also describes how background modulation techniques can be used to isolate the use of colour signals, a prime requirement in colour vision testing.

A further illustrative test (known generally in the art as an "advanced vision test") is described in a paper entitled "'Double-blindsight' revealed through the processing of color and luminance contrast defined motion signals" by J. L. Barbur (published in: Progress in Brain Research, 2004, Volume 144, pages 243 to 259). This paper described a motion contrast sensitivity (MCS) test that involves the measurement of the smallest luminance contrast that a user needs to see motion and to discriminate correctly the direction of movement.

The foregoing tests are usually undertaken by displaying computer generated images to a subject via a very high quality and high definition monitor, typically a cathode ray tube. The subject attends to the images presented on the display and operates an input device, typically a selection of switches, in response to the stimuli they are observing on the screen. For example, in a test where the user might be required to identify the location of a gap in a Landolt C optotype, the input device may comprise four switches and the user may be instructed to operate the switch that corresponds to the quadrant of the image (top left, bottom left, top right or bottom right) in which the gap in the Landolt C optotype is located. Once the user has responded to the particular image being displayed, a new image is presented for the user to respond to, and this process continues until a range of images have been presented and corresponding user responses have been noted. The computer program then determines the user's visual performance based on their responses to the images displayed.

Whilst these systems have been shown to be effective in vision testing and have enabled subjects' visual performance to be accurately assessed, it is generally the case that the equipment (in particular the display) required to perform these tests is typically very expensive and hence tends only to be accessible at selected hospitals or research centres. As the equipment tends not to be universally provided, users can often live a relatively long way from the nearest hospital that has the facility to undertake these tests. Travelling to these hospitals is not too much of a problem for able-bodied users, but can be problematic for less able users who cannot travel so easily. The use of such tests for mass screening of diseases of the eye is therefore very limited.

It is also the case that in less developed regions of the world the cost of the equipment is such that the majority of hospitals simply do not have the funds available to acquire the equipment they would need to implement these tests. One unfortunate consequence of this is that many users continue to endure conditions that could perhaps be treated if their vision were to be properly investigated.

It would be highly advantageous, therefore, if a less expensive solution could be proposed, which solution would be more affordable and hence more accessible to users as it would be more likely to be implemented on a wider scale.

However, whilst an easier and less expensive implementation of such tests would undoubtedly be an improvement to existing arrangements, there will still be those users for whom travel is impossible and those hospitals that are still unable to afford the equipment.

Such problems could be mitigated if a testing system could be devised that utilised commonly available visual equipment (such as a computer monitor for example) for the display of tests to users, as users would then be able to undertake the tests using their own equipment and in their own homes. However, the problem here is that the tests are carefully designed to have particular visual characteristics, and it would be very difficult to ensure that reproduced tests still have those characteristics when the visual equipment used for the purpose is likely to differ widely from user to user.

The present invention has been conceived with the aim of addressing one or more of the aforementioned problems.

SUMMARY OF THE INVENTION

To this end, a presently preferred embodiment of the present invention provides advanced vision testing apparatus comprising: a display; means for determining the performance characteristics of said display; means for adapting a vision test in accordance with said determined performance characteristics so that the test is faithfully displayed on said display; means for displaying said adapted test to a user; and means for registering user input in response to said displayed test.

In a particularly preferred embodiment, the apparatus further comprises means for storing the subject's results. The apparatus may comprise one or more of the following: means for detecting any statistically significant changes (in a subject's results) over time; means for diagnosing systemic diseases or specific diseases of the eye from the pattern of results obtained from several vision tests.

Another embodiment of the invention relates to vision testing apparatus comprising: a local display; means for obtaining data characterising the performance characteristics of said local display; means for displaying to a user at said local display, a vision test that comprises an adaptation of a reference vision test; means for registering user input in response to said displayed vision test; and means for providing the user with the results of said displayed test; wherein said reference vision test comprises a test that is optimised for display on a high quality display, and the vision test for display at said local display is obtained by adapting said reference test in accordance with said characterising data so that the vision test displayed on said local display is a faithful reproduction of said reference test.

Preferably, the apparatus comprises a communications interface configured for transmitting information to and receiving information from a remote processing centre. The remote processing centre may comprise a store for reference vision tests.

The remote processing centre may comprise means for adapting reference vision tests in accordance with data characterising the performance characteristics of a remote display.

The adapting means may be configured to adapt a selected reference vision test in accordance with received data characterising the display of a remote vision testing apparatus to thereby generate an adapted vision test for viewing at said remote testing apparatus, and to send said adapted vision test to said remote vision testing apparatus for display.

Preferably, the testing apparatus is configured to send registered user input to said remote processing centre. The remote processing centre may comprise means for analysing registered user input received from said remote processing centre, and for generating results for transmittal to said remote testing apparatus and provision to said user.

The results may comprise a diagnosis that has automatically been generated based on the analysis of said registered user input. The remote processing centre may comprise a store for registered user input, and means for storing received registered user input pertaining to a completed test.

The remote processing centre may comprise means for analysing stored user input pertaining to a test that has been completed by a user on several occasions, and for identifying trends in said user input.

The vision testing apparatus may be configured to receive selected reference vision tests from said remote processing centre. The vision testing apparatus may comprise means for adapting reference vision tests in accordance with the data characterising the performance characteristics of the local display.

The adapting means may be configured to adapt a selected reference vision test in accordance with said characterising data to thereby generate the adapted vision test for viewing at said local display.

The testing apparatus may comprise means for analysing registered user input and for generating results for display to said user. The results may comprise a diagnosis that has automatically been generated based on the analysis of said registered user input. The testing apparatus may comprise means for sending registered user input to said remote processing centre, and wherein said remote processing centre comprises a store for registered user input, and means for storing registered user input pertaining to a completed test in said store. The remote processing centre may comprise means for analysing stored user input pertaining to a test that has been completed by a user on several occasions, and for identifying trends in said user input.

The testing apparatus may comprise means for retrieving, from said remote processing centre store, stored user input pertaining to a test that has been completed by a user on several occasions; and means for analysing said retrieved user input to identify and trends therein.

The adapting means may be configured to calculate, based on said characterising data, the luminances of red, green and blue display primaries that are required for the faithful display of the luminance and chromaticity triplets of said reference test. The adapting means may be configured to correct for back-scatter within said display.

In a particularly preferred arrangement, said communications network comprises an internet.

The means for registering user input may comprise one or more buttons each operable by a user to generate a signal. Preferably the means for registering use input comprises a housing having a front face and at least four buttons arranged generally in a square projecting therefrom.

The means for obtaining characterising data may include a plurality of photoreceptors. The photoreceptors may be provided within a housing that is adapted to be placed adjacent to a front face of said display, the photoreceptors being arranged in said housing to capture light from said front face. The housing may include a clip that is configured to locate on a portion of said display to properly locate said housing with respect to said display.

Another embodiment of the present invention relates to a method of testing vision, the method comprising: obtaining data characterising the performance characteristics of a local display; adapting a reference vision test in accordance with said characterising data to generate an adapted vision test that is a faithful reproduction of said reference test when displayed on said local display; displaying said adapted vision test to a user at said local display; registering user input in response to said displayed adapted vision test; generating a set of results based on said registered user input; and providing said results to the user.

Yet another embodiment of the present invention relates to a vision testing system comprising a vision test web-server and a local vision testing apparatus that can each communicate one with the other via an internet, wherein: the local vision testing apparatus comprises: a local display; means for obtaining data characterising the performance characteristics of said local display; means for displaying to a user at said local display, a vision test that comprises an adaptation of a reference vision test; means for registering user input in response to said displayed vision test; means for providing the user with the results of said displayed test; and a communications interface for web-based communications with said web-server; the vision test web-server comprises: a store for reference vision tests; means for adapting a selected vision test with data characterising the local display of said vision test apparatus; means for sending said adapted vision test to said local vision testing apparatus for display to a user; means for generating a set of results based on registered user input received from said local vision testing apparatus; and means for sending said results to said local vision testing apparatus.

Further preferred features are set out in the claims, and other aspects, aims, embodiments and advantages of the teachings of the invention are set out in the following detailed description and elsewhere in the present application.

BRIEF DESCRIPTION OF THE DRAWINGS

Various aspects of the teachings of the present invention, and arrangements embodying those teachings, will hereafter be described by way of illustrative example with reference to the accompanying drawings, in which.

DETAILED DESCRIPTION OF PREFERRED EMBODIMENTS

Figure 1:
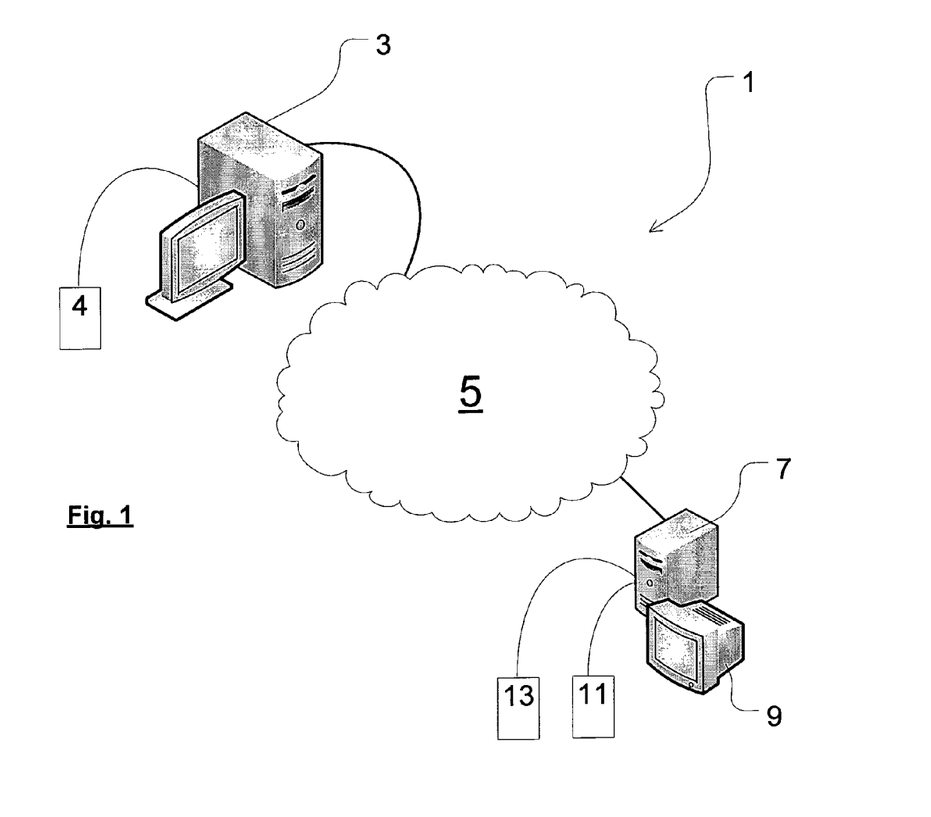
FIG. 1 is a schematic representation of a system according to the present invention.

Referring now to FIG. 1, there is shown an illustrative embodiment of the optometric system 1 according to a preferred embodiment of the present invention.

The system comprises a computing resource, such as a personal computer, that is configured as a test server 3 operable to generate vision tests for display to a user. The server is coupled to a data store 4 (comprising, for example, one or more hard disk drives) in which one or more reference visual tests are stored, each of those reference visual tests comprising a plurality of images that make up a given visual test, the images and the test as a whole being optimised for display on a high quality display with performance characteristics as close as possible to those of an ideal display.

The test server 3 is coupled by way of a communications network 5 to a second computing resource, such as a personal computer, that is configured as a user terminal 7. The user terminal is coupled to a display device 9 (typically a non-ideal display device), such as a cathode ray tube (CRT) or LCD (liquid crystal display), and is configured to display test images received from the test server 3 to a user (not shown). The user terminal is connected to a user input device 11 for the input of user responses to displayed stimuli, and to a calibration detector 13 that is used (in a manner that will later be described) to determine the visual properties of the particular display device 9 that is coupled to the terminal 7.

Information characterising the visual properties of the display is sent to the server 3, and the test server 3 is configured to adapt the appropriate reference test images for display to the user in accordance with the received information so that the test images to be viewed by the user at the display device 9 have a chromaticity and luminance that causes the displayed test images to be a faithful reproduction of the images of the reference test.

The network 5 may comprise any one or more types of communication networks. In one arrangement the network may comprise a local or wide area network (LAN or WAN), and in another particularly preferred arrangement the network may comprise an internet such as the world wide web. This latter arrangement is particularly preferred as it raises the possibility of users in less developed countries being provided with access to leading diagnostic techniques commonly employed in more developed countries.

If the system is implemented via the world wide web, then the server 3 may comprise a webserver to which the client terminal can connect and run a test in a window in a web browser. In an alternative arrangement that is preferred where bandwidth may be limited, tests can be downloaded from the server for local execution and display at the user terminal.

Figure 2:
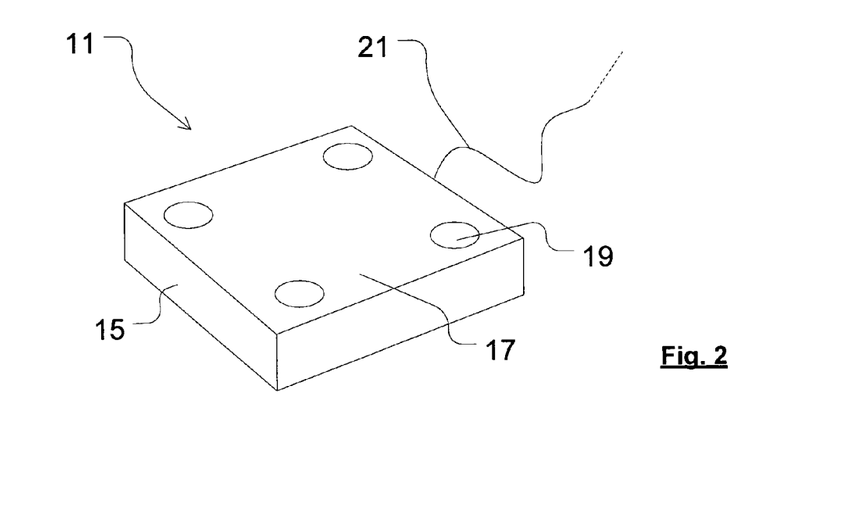
FIG. 2 is a schematic representation of a user response device.

Referring now to FIG. 2, the user response device 11 comprises a housing 15 having a top surface 17 through which, in this instance, four buttons 19 project. The response device includes control circuitry that is operable to detect when the buttons are pressed by a user and generate a signal indicative of those button presses for transfer to the terminal 7 via the cable 21. In this arrangement the buttons correspond to four regions of a test image display area—namely, a top left region, a bottom left region, a top right region and a bottom right region.

In use a subject may, for example, be shown an image of a Landolt C optotype and be asked to identify whether the gap is in the top left, bottom left, top right or bottom right quadrant of the display by pressing the corresponding button on the user response device. For most vision tests, four buttons will suffice, although five buttons (with the fifth button being located at the centre of the square formed by the other four buttons) may also be employed. Ultimately, the number of buttons provided will depend on the test, and as such it will be appreciated that a greater or lesser number of buttons may instead be provided if desired.

Figure 3:
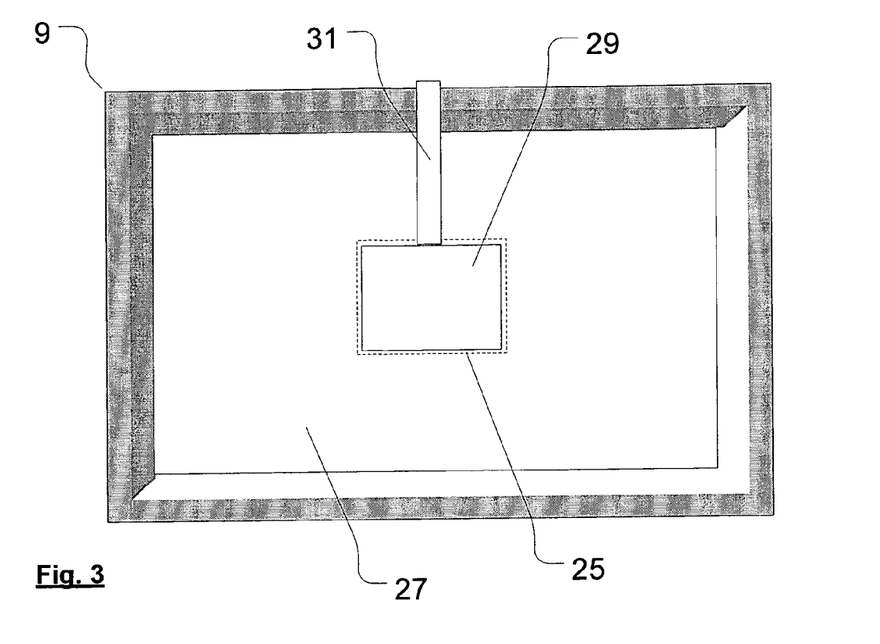
FIG. 3 is a schematic representation of a display screen and installed calibration detector.

Referring now to FIG. 3, there is shown a display device 9 (in this instance a CRT) that defines a viewing area 27. As is known in the art, the screen of a CRT is made up of a number of discrete picture elements or pixels, and in the limiting case each pixel of a color display screen consists of three phosphors each driven by separate electron guns. Ideally, activation of one of these guns causes a single class of phosphor to emit light, and the luminance of a given pixel is defined in terms of three values (one for each electron gun) that are used to alter the voltage of the electron guns in the display, and hence the "colour" of that pixel.

Figure 4:
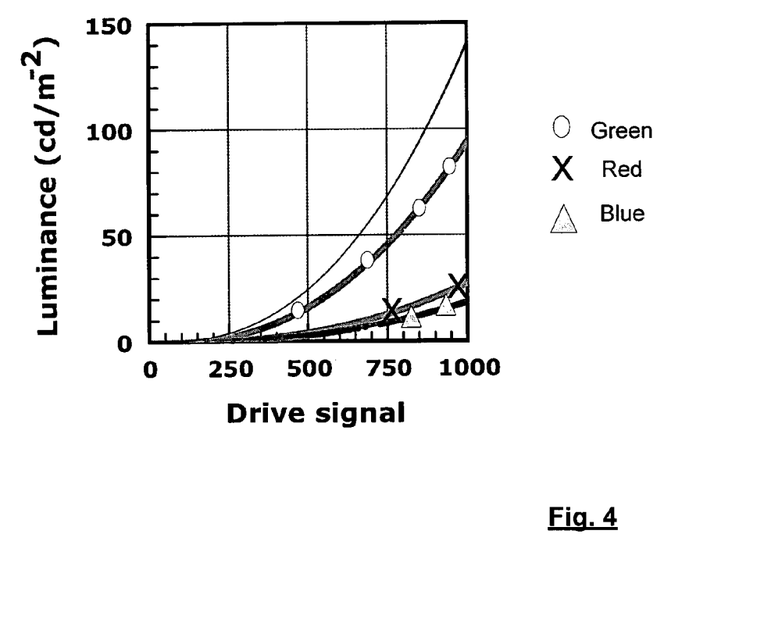
FIG. 4 is a schematic plot of display luminance versus drive signal.

In an ideal display pixel luminance would be linearly related to drive voltage. However, in practice (as illustrated in FIG. 4) the luminance of the red, green and blue primaries is a non-linear function of the drive signals applied, in this instance, to the red, green and blue electron guns within the CRT. In general, the degree of non-linearity increases as the quality of the display decreases.

A further problem is that the luminance of the display is non-uniform over the viewing area 27. This is particularly the case, and becomes progressively more apparent, away from a generally central viewing region 25 towards the edge of the viewing area 27.

These non-linearities and non-uniformities tend to have little effect on the image when the display is used for conventional purposes, but they can be of great significance when the display is used to display test images of the type described herein, as successive images may only be very slightly different from one another, and if the display is such that those differences cannot be determined by the viewer then the accuracy of the test will be adversely affected.

To investigate the performance of the display a detector assembly is provided to enable the output of the display to be measured. The detector assembly is plugged into the subject's terminal to enable the capture of data from it, and comprises a housing 29 within which a plurality of light detectors are provided, the detectors being orientated to capture light emitted by the display. The detector assembly further comprises a mounting arm 31 that is adapted to engage with the top of the monitor and sized so as to correctly locate the photometers in the central viewing region 25 of the display.

To reduce the impact of non-uniformities across the surface of the viewing area, the system of the present invention is configured so that test images are displayed only within the generally central viewing region 25 of the viewing area 27 (within which region the non-uniformities are lowest).

By configuring the display in this way, the impact of these surface non-uniformities can be reduced. However, the present inventors have found that the luminance of the relatively large remainder of the viewing area 27 (in which no test images are displayed) can have a direct effect on the luminance of images displayed within the central viewing region. Investigations have suggested that this variance in luminance may result from back-scatter of photons within the display, and to address this unwanted scattering the present inventors have devised a means for determining the extent to which a displayed test image will be affected by back scatter within the display. On some visual displays, the calibration curves that describe the relation between the light output of each gun at the centre of the display and the corresponding voltage drive signal vary systematically with the overall luminance of the whole background field, and if advanced vision tests are to be implemented on visual displays it is preferred for these potential artefacts to be accounted for.

Figure 5A:
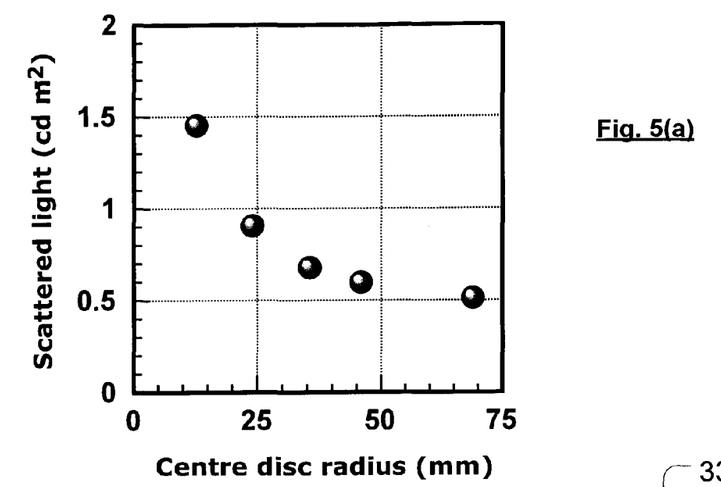
FIG. 5a is a schematic plot of scatter luminance versus disc radius.
Figure 5B:
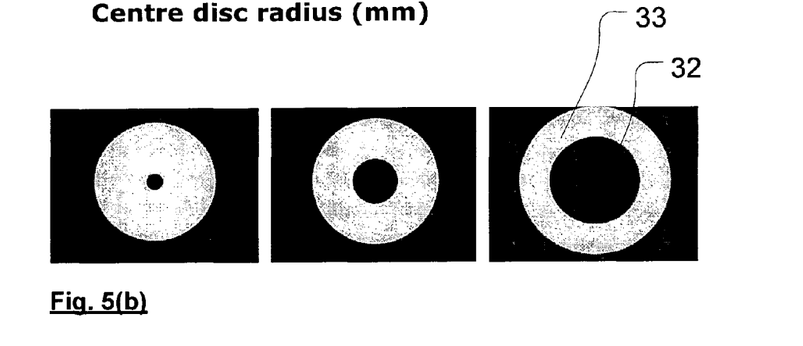
FIG. 5b is a schematic representation of three illustrative images used for determination of a plot of the type depicted in FIG. 5a; a Calibration Curve shown in FIG. 5 (c)
Figure 5C:
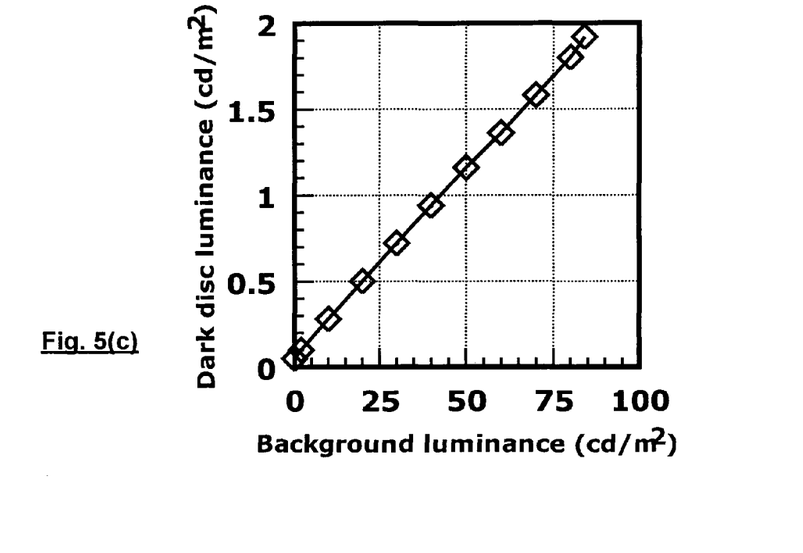

Determination of back scatter is accomplished by displaying a series of images of the type shown in FIG. 5b which comprise a dark central region 32 and a lighter background region 33, and measuring the extent to which the luminance of the dark central region is affected as the size of the lighter background region is varied. FIG. 5a is a plot of scattered light versus centre disk radius, and it is clear from this figure that as the radius of the central disk (in FIG. 5b) reduces so the scattered light increases and the luminance of the central darker region is increased. From this relationship it is possible to derive a calibration curve, shown in FIG. 5c, indicating the relationship between background luminance and the luminance of the dark central region. Once this relationship has been established, the test image can be corrected for internal scatter within the display for a background that has the luminance of the background employed in the particular test being undertaken.

To reduce the impact of non-linearities in the relationship between drive voltage and luminance, the background surrounding the viewing region is set to have a luminance and chromaticity which is at least similar to that employed in the test that the user is to undertake, and the luminance is measured as each of the electron guns are driven through the entire voltage supply range to derive the Luminance versus Drive signal curves of the type shown in FIG. 4. If the test to be undertaken should involve the display of backgrounds at different luminances, then this step of the calibration process is repeated to derive, for each luminance, a luminance versus drive signal curve for each of the electron guns.

In a next step the spectral radiance (i.e. the amount of light (or radiant flux) of a given wavelength per unit solid angle per unit area of the display that is emitted in a given direction) is measured for each display primary light for the purpose of calculating the chromaticity co-ordinates (x, y) of each primary. This is accomplished without a surround so as to ensure that the light emitted comes only from one primary. Chromaticity co-ordinates, as is known in the art, comprise two numbers that together specify the ratio of cone photoreceptor signals in the eye generated in response to light of given spectral composition.

The calibration data (i.e., the chromaticity co-ordinates and the luminance versus drive voltage curve for each primary) are then used in standard colorimetric equations (for examples of the equations, see G. W. Wyszecki and W. S. Stiles. *"Color Science—Concepts and Methods, Quantitative Data and Formulae"*, New York: John Wiley & Sons, 1982— the contents of which are incorporated herein in its entirety) to calculate the luminances of the red, green and blue primaries needed to reproduce any specified luminance, chromaticity triplet (i.e., L, x, y) within the limits imposed by the display device.

Once this procedure has been completed, it is then possible to produce visual stimuli on displays with the accurate control of luminance and chromaticity that is needed for the various tests of visual performance described herein.

Determination of the performance of the display is accomplished when the display is first registered for use in the system, and once the calibration data for that display have been determined they are stored on the server in association with a special identifier that identifies uniquely the particular display and computer combination at the user terminal. In a preferred arrangement, each time a given user terminal is used, a check is made as to whether a unique identifier retrieved from that terminal matches that stored at the server for this terminal. If the identifier retrieved from the terminal should be different to that stored at the server, then the terminal displays a message indicating that the terminal display must be calibrated before the test can continue. Recalibration is also recommended to the user depending on the date of the last recalibration.

Figure 6:
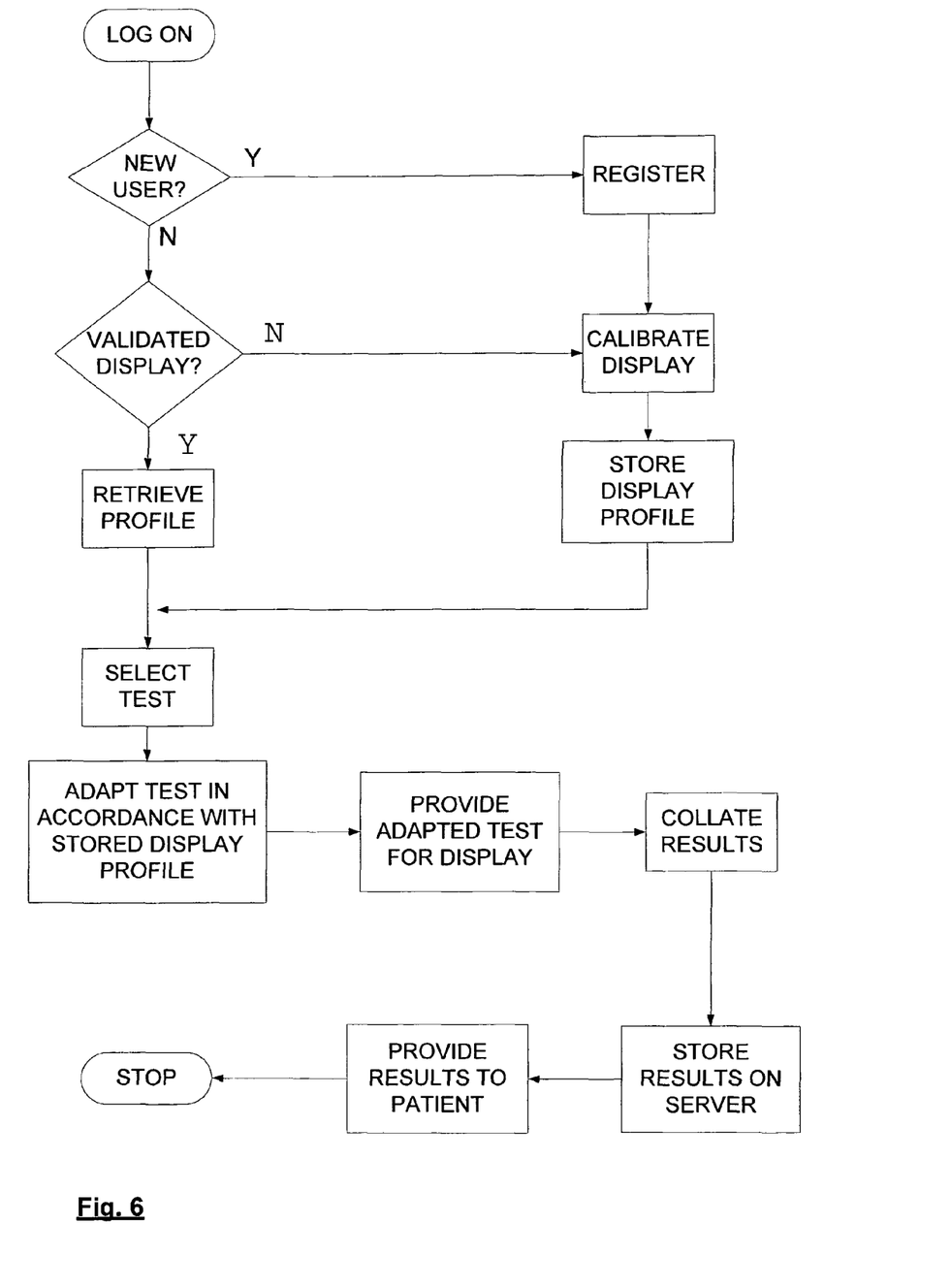
FIG. 6 is a schematic representation of the steps of a method of vision testing.

In one envisaged implementation, described hereafter in connection with FIG. 6, the teachings of the present invention may be implemented as a service to which an ophthalmologist, optometrist or private individual may subscribe. In the intended implementation, the subscriber would receive a compact disc (or other data carrier) carrying software to implement the teachings of the invention, instructions on monitor calibration and the use of each program, a display calibration device and a user input device.

The subscriber executes the supplied program to log onto the service (step 100) using a web browser and if the subscriber has not used the service before they are requested to register their computer with the server (step 102), following which the subscriber's computer display is calibrated using the display calibration device and procedure provided (step 104), following which the characteristics for that display are stored on the web server (step 106). The web server detects whether each profile stored replaces an existing profile or is the result of calibrating a new display. As aforementioned a calibration profile is identified by the Global Unique Identifier (GUID) assigned to the monitor (and the graphics card which runs it) by Microsoft Windows. Should a display need to be replaced for any reason, the replacement will need to be calibrated (and the web server detects this).

If the subscriber has used the service before, then the subscriber's display is validated (by comparing the GUID of that display with the GUID stored for that subscriber) (step 108). If this validation step should fail (for example because the subscriber has changed their display), then the subscriber is asked to complete the calibration process (step 104). If the validation step should be successfully passed, the profile for that display is retrieved (step 108).

A test to be undertaken is then selected (step 110), and while the server is generating the stimuli which will be used during the corresponding test (in particular whilst the server is adapting the stored reference test in accordance with the profile for the subscriber's display), the subscriber is presented with a form to fill in giving details for the person undertaking the test. This information is stored by the web server so that if that person should be re-tested it is only necessary to enter sufficient details to identify them (typically just their name).

Short video clips for the stimuli of an illustrative test to be performed are generated by the web server from the associated reference test by adapting that reference test in accordance with monitor calibration profile (step 112). During the test itself, the subscriber is asked to view a series of these clips that are streamed to the terminal (step 114) and to indicate, for example, in which direction (NE, NW, SE or SW) a coloured target moved. In the case of contrast acuity assessment, the subject is required to indicate the orientation of the target. In a more complex visual test that involves five buttons and five stimuli (i.e., one in each quadrant and one along the line of sight, see fig. xx) the subject's task may be to indicate which of the five stimuli contains a gap or which of the five stimuli flickers by pressing the appropriate response button to indicate the stimulus location. If the subject is not sure where the stimulus is located or cannot judge the direction of motion of the stimulus, the subject's instruction is to guess by pressing any of the buttons. This response can be entered either using the user input device or by clicking on-screen buttons displayed for this purpose. The web server will then display the next video clip until the test is completed and the measurement is made (step 116). The web server will then use a knowledge-based system to interpret the experimental measurements and suggest diagnosis (step 118). The results of several tests may be stored on the server and in some instances the results from more than one test are utilised for diagnosis.

The results of the test are stored on the web server and can be retrieved at a later date, if so desired. The server also has the ability to display significant longitudinal changes in a subject's response. This can be particularly useful in the detection of significant changes in performance even though the subject's responses remain within a normal range of expected performances. By this we mean that even though a subject's visual performance falls within the "normal range" established from measurements of a large number of "normal subjects", a subject can have a statistically significant increase in thresholds (on re-testing months later), even though the new thresholds still fall within the "normal range".

The system described herein may also usefully be employed to monitor disease progress or the effect of treatment in users with diagnosed conditions. Results can also be saved on the local computer in XML format (or any other format) for further processing. A number of reports can also be generated in PDF format suitable for printing.

As will now be apparent, the teachings of the present invention provide a means whereby vision testing (in particular, testing of the type known in the art as "advanced testing") can be undertaken without the expense associated with purchasing dedicated processing machinery, and if necessary in the comfort of a user's home.

It will be appreciated that whilst various aspects and embodiments of the present invention have heretofore been described, the scope of the present invention is not limited to the particular arrangements set out herein and instead extends to encompass all arrangements, and modifications and alterations thereto, which fall within the scope of the appended claims. For example, it should be noted that the teachings of the present invention are not limited soley to CRT displays, but may instead be adopted for any other type of display, such as a liquid crystal display (LCD) or a surface-conduction electron-emitter display (SED).

It will also be apparent to persons skilled in the art that the physical location of functional components of the system described herein may be altered without departing from the scope of the invention. For example, whilst it is preferred that the server is configured to adapt tests and send adapted tests to the local user terminal for display, it will be apparent that the vision tests could alternatively be adapted at the local terminal. This could be accomplished with the local terminal computing the adaptations that need to be made to the reference test, or alternatively, the adaptations could be computed by the server and then provided to the user terminal for application to a given reference test.

It should also be noted that whilst the accompanying claims set out particular combinations of features described herein, the scope of the present invention is not limited to the particular combinations hereafter claimed, but instead extends to encompass any combination of features herein disclosed.

The invention claimed is:

1. Vision testing apparatus comprising:
    a local display;
    means for obtaining data characterising the performance characteristics of said local display;
    means for displaying to a user at said local display, a vision test that comprises an adaptation of a reference vision test;
    means for registering user input in response to said displayed vision test;
    means for providing the user with the results of said displayed test; and
    a communications interface configured for transmitting information to and receiving information from a remote processing centre;
    wherein:
    said reference vision test comprises a test that is optimised for display on a high quality display, and the vision test for display at said local display is obtained by adapting said reference test in accordance with said characterising data so that the vision test displayed on said local display is a faithful reproduction of said reference test;
    said testing apparatus is configured to send registered user input to said remote processing centre; and
    said remote processing centre comprises means for analysing registered user input received from said testing apparatus, and for generating results for transmittal to said remote testing apparatus and provision to said user; said results comprising a diagnosis that has automatically been generated based on the analysis of said registered user input.

2. Apparatus according to claim 1, wherein said remote processing centre comprises a store for reference vision tests.

3. Apparatus according to claim 2, wherein said remote processing centre comprises means for adapting reference vision tests in accordance with data characterising the performance characteristics of a remote display.

4. Apparatus according to claim 3, wherein said adapting means is configured to adapt a selected reference vision test in accordance with received data characterising the display of a remote vision testing apparatus to thereby generate an adapted vision test for viewing at said remote testing apparatus, and to send said adapted vision test to said remote vision testing apparatus for display.

5. Apparatus according to claim 1, wherein said remote processing centre comprises a store for registered user input, and means for storing received registered user input pertaining to a completed test.

6. Apparatus according to claim 5, wherein said remote processing centre comprises means for analysing stored user input pertaining to a test that has been completed by a user on several occasions, and for identifying trends in said user input.

7. Apparatus according to claim 1, wherein said vision testing apparatus is configured to receive selected reference vision tests from said remote processing centre.

8. Apparatus according to claim 7, wherein said vision testing apparatus comprises means for adapting reference vision tests in accordance with the data characterising the performance characteristics of the local display.

9. Apparatus according to claim 8, wherein said adapting means is configured to adapt a selected reference vision test in accordance with said characterising data to thereby generate the adapted vision test for viewing at said local display.

10. Apparatus according to claim 7, wherein said testing apparatus comprises means for analysing registered user input and for generating results for display to said user.

11. Apparatus according to claim 10, wherein said results comprise a diagnosis that has automatically been generated based on the analysis of said registered user input.

12. Apparatus according to claim 1, wherein said means for obtaining characterising data includes a plurality of photoreceptors.

13. Apparatus according to claim 12, wherein said photoreceptors are provided within a housing that is adapted to be placed adjacent to a front face of said display, the photoreceptors being arranged in said housing to capture light from said front face.

14. Vision testing apparatus comprising:
a local display;
means for obtaining data characterising the performance characteristics of said local display;
means for displaying to a user at said local display, a vision test that comprises an adaptation of a reference vision test;
means for registering user input in response to said displayed vision test;
means for providing the user with the results of said displayed test; and
means for sending registered user input to a remote processing centre, said remote processing centre comprising a store for registered user input, and means for storing registered user input pertaining to a completed test in said store;
wherein:
said reference vision test comprises a test that is optimised for display on a high quality display, and the vision test for display at said local display is obtained by adapting said reference test in accordance with said characterising data so that the vision test displayed on said local display is a faithful reproduction of said reference test.

15. Vision testing apparatus comprising:
a local display;
means for obtaining data characterising the performance characteristics of said local display;
means for displaying to a user at said local display, a vision test that comprises an adaptation of a reference vision test;
means for registering user input in response to said displayed vision test;
means for providing the user with the results of said displayed test; and
means for sending registered user input to a remote processing centre, said remote processing centre comprising a store for registered user input, and means for storing registered user input pertaining to a completed test in said store;
wherein:
said reference vision test comprises a test that is optimised for display on a high quality display, and the vision test for display at said local display is obtained by adapting said reference test in accordance with said characterising data so that the vision test displayed on said local display is a faithful reproduction of said reference test; and
either (a) said remote processing centre comprises means for analysing stored user input pertaining to a test that has been completed by a user on several occasions, and for identifying trends in said user input; or
b) said testing apparatus comprises means for retrieving, from said remote processing centre store, stored user input pertaining to a test that has been completed by a user on several occasions; and means for analysing said retrieved user input to identify trends therein.

* * * * *